United States Patent [19]
Briggs et al.

[11] Patent Number: 4,479,818
[45] Date of Patent: Oct. 30, 1984

[54] SURGICAL DRAINAGE BAGS

[75] Inventors: Peter J. Briggs, Sompting; Kenneth J. Brooks, Lancing, both of England

[73] Assignee: Matburn (Holdings) Limited, London, England

[21] Appl. No.: 375,652

[22] Filed: May 6, 1982

[30] Foreign Application Priority Data

May 7, 1981 [GB] United Kingdom ................ 8113942
Sep. 14, 1981 [GB] United Kingdom ................ 8127699

[51] Int. Cl.³ ............................................. B01D 50/00
[52] U.S. Cl. .................................. 55/385 C; 604/333
[58] Field of Search ..................... 55/385 C, 279, 372, 55/387, 374, 316, 503, 505, 507, 509; 604/332-338, 339-344; 128/760, 766, 767, 768

[56] References Cited

U.S. PATENT DOCUMENTS

| | | | |
|---|---|---|---|
| 2,994,404 | 8/1961 | Schifferly | 55/316 |
| 3,690,320 | 9/1972 | Riely | 604/336 |
| 3,782,083 | 1/1974 | Rosenberg | 55/501 |
| 4,120,715 | 10/1978 | Ockwell et al. | 604/333 |
| 4,268,286 | 5/1981 | Steer et al. | 55/385 C |
| 4,356,012 | 10/1982 | Hofstetler | 55/385 C |

FOREIGN PATENT DOCUMENTS

| | | | |
|---|---|---|---|
| 2900806 | 7/1980 | Fed. Rep. of Germany | 604/334 |
| 743535 | 1/1956 | United Kingdom | 604/334 |
| 2031282 | 4/1980 | United Kingdom | 604/335 |

Primary Examiner—Bernard Nozick
Attorney, Agent, or Firm—McAulay, Fields, Fisher, Goldstein & Nissen

[57] ABSTRACT

A surgical drainage bag has a vent opening in a rear wall of the bag. A first mount is attached to the rear wall of the bag and has an opening registering with the opening in the rear wall. A second mount has a tubular plug which is a press fit in the opening in the first mount and communicates with a recess containing a filter element.

8 Claims, 4 Drawing Figures

SURGICAL DRAINAGE BAGS

BACKGROUND OF THE INVENTION

Surgical drainage bags of the kind used by patients who have had colostomy or ileostomy operations are commonly called ostomy bags. They are used to receive waste material from the stoma of the patient. Flatus will, of course, also pass into the bag and for this reason such bags are commonly provided with venting means to enable the flatus to escape. It is known to provide the venting means with a filter to remove undesirable odours. For example, an ostomy bag with a venting means is described in published United Kingdom Patent Specification No. 15964396.

An object of the present invention is to provide an improved filter for such a bag and a bag with a filter which can easily be replaced by the patient as desired and which is adequately leakproof.

BRIEF SUMMARY OF THE INVENTION

The present invention provides an ostomy bag which has in one wall a vent opening through which flatus can pass from the interior of the bag, the vent opening being provided with a filter through which the flatus can pass, wherein a first mount is secured to the said wall of the bag and has an opening communicating with the vent opening and a second mount has a tubular vent plug which is removably fitted in the opening in the first mount and also has a filter. The filter may be composed of one or more filter elements, preferably two.

According to another aspect of the invention, there is provided a filter for an ostomy bag comprising a first mount which is adapted to be secured to a wall of the bag, and has an opening adapted to be registered with a vent opening of the bag, and a second mount having a tubular vent plug adapted to engage in the opening in the first mount, and leading into a recess in the mount in which a filter is located.

BRIEF DESCRIPTION OF THE ACCOMPANYING DRAWINGS

DESCRIPTION OF SOME EMBODIMENTS

Figure 1:
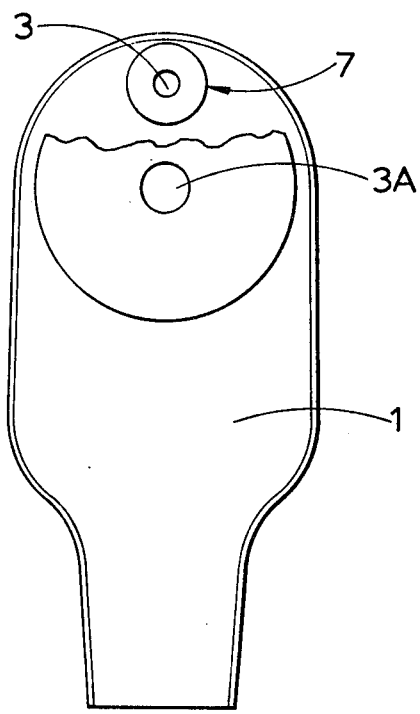
FIG. 1 is a schematic view of an ostomy bag.
Figure 2:
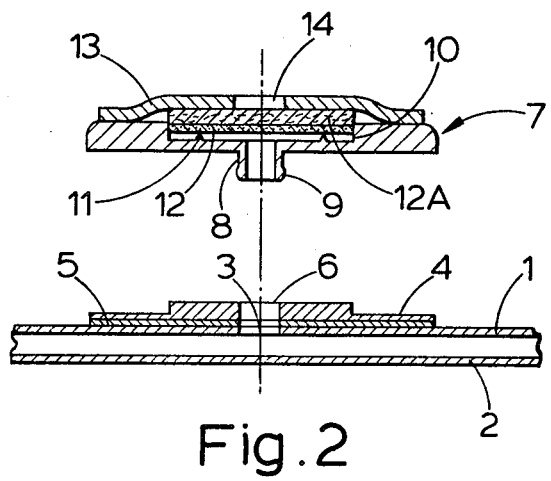
FIG. 2 is an exploded sectional view of a portion of a bag having one embodiment of a filter arrangement according to the invention.

The ostomy bag illustrated in FIGS. 1 and 2 is primarily intended for use by ileostomy patients. It comprises two walls 1 and 2 of flexible sheet plastics material seamed together at the edges. When the bag is in use, the wall 1 is the rear wall of the bag intended to be closest to the body of the patient. The rear wall 1 has an inlet opening 3A intended to communicate with the stoma of a patient and a vent opening 3 which is positioned above the inlet opening 3A and near the top of the bag when the bag is in use. A female mount 4 made of a thermoplastics material is secured to the outside of the rear wall 1 of the bag conveniently by a doublesided adhesive ring 5, or if desired, by a weld. The female mount 4 has a central passage 6 which registers with the vent opening 3 in the rear wall 1 of the bag.

The female mount 4 is arranged to receive a male mount 7 also of thermoplastics material. The mount 7 includes a tubular plug 8 which is a press fit in the passage 6 of the female mount 4. The tubular plug 8 has an outwardly directed bead 9 to assist in retaining the plug 8 in the passage 6 of the female mount 4, but the mount 7 can be withdrawn by the patient as desired and, if necessary, replaced by another mount 7 or alternatively by a closed plug member. The male mount 7 has a recess 10 at its front. An annular rib 11 is provided on the base of the recess 10. A filter element 12 is located in the recess 10 and is overlaid by a second filter element 12A which is held in position by an adhesive ring 13. The opening 14 in the adhesive ring registers with the tubular plug 8.

Figure 3:
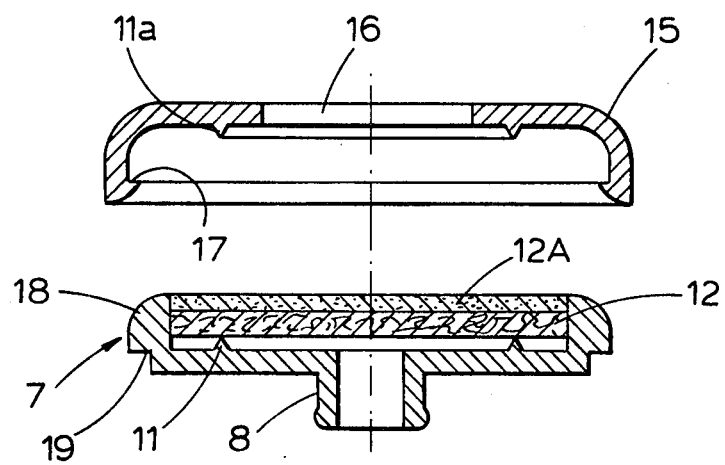
FIG. 3 is an exploded sectional view.
Figure 4:
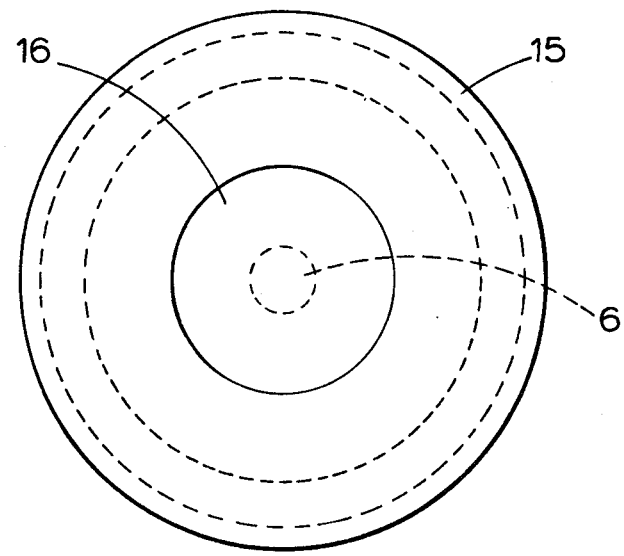
FIG. 4 is a plan view of a male mount forming part of a second embodiment.

In the embodiment illustrated in FIGS. 3 and 4 the male mount is constructed so that instead of the adhesive ring 13, a cap 15 having an opening 16 is provided to hold the filter elements 12, 12A in position. In this embodiment, the skirt of the cap 15 of the male mount 7 has an inwardly turned lip 17. The cap 15 is snap fitted over the base 18 of the mount 7 and the lip 17 engages beneath a shoulder 19 of the base 18 to retain the cap in position with opening 16 in register with the tubular plug 8. An annular rib 11A is provided on the internal surface of the cap which contacts the filter element 12A.

In both embodiments the filter element or elements may be made of activated carbon cloth or may be made of a fibrous material impregnated with activated carbon. Conveniently, but not essentially, the filter may be constructed as described in the published U.K. Patent Specification No. 2076689A.

The said published specification describes a filter for a surgical drainage bag comprising a filter layer of activated carbon cloth through which gases may pass from the interior of the bag, a first layer of gas permeable thermoplastics material in contact with one side of the filter layer, a barrier layer of gas permeable hydrophobic material having one side in contact with the said first layer, a second layer of gas permeable thermoplastics material having one side in contact with the other side of the barrier layer, all the said layers being secured together by a peripheral seal.

Although it is preferred that the filter is composed of two filter elements, a single filter element 12 or more than two filter elements may be used if desired.

When the bag is in use flatus from the interior of the bag will pass through the vent opening 3 and the tubular plug and exit through the filter. The ribs 11 and 11A resist any tendency of the flatus to pass to the periphery of the filter elements 12 and 12A so that the flatus can only exit through the filter.

The male mount 7 can be removed by the patient as desired. For example, if the bag is a drainable bag the removal of the mount 7 facilitates flushing of the bag through the then exposed aperture 3 and passage 6. Furthermore, if the patient requires extra security as when sleeping, the mount 7 can be removed and be replaced by a closed plug member, or by an adhesive disc.

Although in the embodiments described, the vent opening 3 is in the rear wall 1 of the bag, it may if desired be located in the front wall 2.

What is claimed is:

1. An ostomy bag comprising a vent opening in one wall through which flatus can pass from the interior of the bag, said vent opening being provided with a filter system for removing odors from flatus passing there-through, said filter system comprising a first mount secured to said wall of the bag and having a through opening communicating with the vent opening, and a second mount having a tubular vent plug slidably and removably received in said opening in said first mount, an outlet opening in said second mount, and at least one filter element which removes odor in said second mount positioned between said vent plug and said outlet opening.

2. A bag as claimed in claim 1, wherein the second mount is of thermoplastics material and has a recess in which said filter element is located, the said filter element being retained in the recess by a cap fitted on the second mount.

3. A bag as claimed in claim 1, wherein the second mount is of thermoplastics material and has a recess in which said filter element is located, the said filter element being retained by an adhesive ring secured to the second mount.

4. A bag as claimed in any one of claims 1, 2, or 3 wherein means are provided in the second mount to ensure that flatus exits through the filter element and not around the periphery thereof.

5. A bag as claimed in claim 4, wherein the means is an annular rib.

6. A bag as claimed in claim 2, wherein the cap is provided with means to ensure that flatus exits through the filter element and not around the periphery thereof.

7. A bag as claimed in claim 6, wherein the means is an annular rib.

8. A filter system with a bag with a vent opening comprising a first mount which is secured to a wall of the bag, and is provided with a through opening in registration with said vent opening of said bag, and a second mount having a tubular vent plug removably received in the opening in said first mount and in sliding engagement therewith, a recess in said second mount communicating with the vent in said plug, an outlet opening in said second mount, and at least a filter element which removes odors received in said recess and positioned between said vent plug and said outlet opening.

* * * * *